(12) United States Patent
Perrin et al.

(10) Patent No.: US 9,364,313 B2
(45) Date of Patent: Jun. 14, 2016

(54) MEDICAL DEVICE FOR SUPPORTING AN IMPLANT OR PROSTHESIS

(71) Applicant: Protip SAS, Strasbourg (FR)

(72) Inventors: Nicolas Perrin, Schiltigheim (FR); Maurice Berenger, Strasbourg (FR); Andre Walder, L'Hayes-les-Roses (FR)

(73) Assignee: Protip SAS, Strasbourg (FR)

( * ) Notice: Subject to any disclaimer, the term of this patent is extended or adjusted under 35 U.S.C. 154(b) by 1 day.

(21) Appl. No.: 14/361,136

(22) PCT Filed: Nov. 20, 2012

(86) PCT No.: PCT/EP2012/073117
§ 371 (c)(1),
(2) Date: May 28, 2014

(87) PCT Pub. No.: WO2013/079362
PCT Pub. Date: Jun. 6, 2013

(65) Prior Publication Data
US 2015/0094809 A1    Apr. 2, 2015

(30) Foreign Application Priority Data
Nov. 30, 2011  (FR) ...................................... 11 60933

(51) Int. Cl.
*A61F 2/20* (2006.01)
*A61F 2/04* (2013.01)
(Continued)

(52) U.S. Cl.
CPC . *A61F 2/04* (2013.01); *A61B 17/68* (2013.01); *A61B 17/8665* (2013.01); *A61F 2/203* (2013.01); *A61F 2002/046* (2013.01); *A61F 2220/0008* (2013.01); *A61F 2220/0025* (2013.01); *A61F 2220/0033* (2013.01);
(Continued)

(58) Field of Classification Search
CPC ................................... A61F 2/20; A61F 2/203
USPC ............................................................. 623/9
See application file for complete search history.

(56) References Cited

U.S. PATENT DOCUMENTS

| 2,198,241 A | 4/1940 | Brehm |
| 4,374,669 A | 2/1983 | MacGregor |

(Continued)

FOREIGN PATENT DOCUMENTS

| DE | 1791014 A1 | 10/1971 |
| DE | 202004010382 U1 | 11/2004 |

(Continued)

OTHER PUBLICATIONS

International search report dated Jun. 13, 2013 for PCT/EP2013/073117.

(Continued)

*Primary Examiner* — Suzette J Gherbi
(74) *Attorney, Agent, or Firm* — Wilson Sonsini Goodrich & Rosati

(57) ABSTRACT

The invention relates to a medical device for supporting an implant or prosthesis, formed by two parts including one part forming an upper ring (1) which is made from a rigid or semi-rigid solid biocompatible material and another part forming a lower ring (2) which is made from a rigid or semi-rigid, integrable or porous biocompatible material, said device being intended to receive an implant or a removable prosthesis at the upper ring and to be installed in situ by means of the lower ring.

16 Claims, 8 Drawing Sheets

(51) Int. Cl.
*A61B 17/68* (2006.01)
*A61B 17/86* (2006.01)

(52) U.S. Cl.
CPC . *A61F2220/0041* (2013.01); *A61F 2220/0075* (2013.01); *A61F 2250/006* (2013.01)

(56) References Cited

U.S. PATENT DOCUMENTS

| | | | |
|---|---|---|---|
| 4,435,853 A | 3/1984 | Blom et al. | |
| 4,538,607 A | 9/1985 | Saul | |
| 4,550,448 A | 11/1985 | Kenna | |
| 4,911,716 A | 3/1990 | Blom et al. | |
| 5,358,522 A | 10/1994 | Montgomery et al. | |
| 5,391,205 A | 2/1995 | Knight | |
| 5,507,809 A | 4/1996 | Blom | |
| 5,765,560 A | 6/1998 | Verkerke et al. | |
| 5,855,612 A | 1/1999 | Ohthuki et al. | |
| 5,911,756 A | 6/1999 | Debry | |
| 5,957,978 A | 9/1999 | Blom | |
| 6,159,008 A * | 12/2000 | Kumar | A61C 8/0087 433/141 |
| 6,193,751 B1 * | 2/2001 | Singer | A61F 2/20 128/207.16 |
| 6,358,222 B1 | 3/2002 | Grundei | |
| 6,402,515 B1 | 6/2002 | Patti et al. | |
| 6,565,581 B1 | 5/2003 | Spence et al. | |
| 6,666,208 B1 | 12/2003 | Schumacher et al. | |
| 6,913,623 B1 | 7/2005 | Zhu | |
| 7,025,784 B1 * | 4/2006 | Blom | A61F 2/20 623/14.11 |
| 7,166,128 B1 | 1/2007 | Persson | |
| 7,998,200 B2 | 8/2011 | Nelson | |
| 8,167,936 B2 * | 5/2012 | Kurian | A61F 2/2427 623/2.41 |
| 8,551,168 B2 | 10/2013 | Debry et al. | |
| 8,603,388 B2 * | 12/2013 | Debry | A61C 8/0012 419/2 |
| 8,800,564 B2 * | 8/2014 | Scott | A61M 16/0468 128/207.14 |
| 2002/0156527 A1 | 10/2002 | Persson | |
| 2002/0193879 A1 | 12/2002 | Seder et al. | |
| 2005/0025656 A1 | 2/2005 | Bhaduri et al. | |
| 2005/0171602 A1 | 8/2005 | Goldberg et al. | |
| 2006/0276893 A1 | 12/2006 | Nelson | |
| 2008/0027473 A1 * | 1/2008 | Bjerken | A61B 17/0469 606/157 |
| 2008/0050452 A1 | 2/2008 | Chen et al. | |
| 2008/0072912 A1 * | 3/2008 | Scott | A61M 16/0468 128/207.14 |
| 2009/0026660 A1 | 1/2009 | Nelson et al. | |
| 2009/0043386 A1 | 2/2009 | Persson | |
| 2009/0253099 A1 * | 10/2009 | Debry | A61L 27/56 433/174 |
| 2010/0227294 A1 * | 9/2010 | Takagi | A61C 8/005 433/174 |
| 2011/0106251 A1 | 5/2011 | Debry et al. | |
| 2011/0264214 A1 | 10/2011 | Nelson | |
| 2012/0215306 A1 | 8/2012 | Fagan et al. | |
| 2013/0072759 A1 * | 3/2013 | Li | A61B 19/087 600/208 |
| 2014/0288648 A1 | 9/2014 | Walder et al. | |
| 2014/0303745 A1 * | 10/2014 | Anderson | A61B 17/68 623/23.54 |
| 2015/0238659 A1 | 8/2015 | Dove et al. | |
| 2015/0305860 A1 | 10/2015 | Wang et al. | |

FOREIGN PATENT DOCUMENTS

| | | |
|---|---|---|
| DE | 202007000655 U1 | 3/2007 |
| EP | 0651980 A2 | 5/1995 |
| EP | 0815807 A1 | 1/1998 |
| EP | 0856299 A1 | 8/1998 |
| EP | 1736119 A2 | 12/2006 |
| EP | 1937185 B1 | 2/2010 |
| EP | 1940480 B1 | 6/2010 |
| EP | 2240120 B1 | 7/2012 |
| FR | 1102694 A1 | 10/1955 |
| FR | 1211841 A | 3/1960 |
| FR | 2559067 A1 | 8/1985 |
| FR | 2891133 A1 | 3/2007 |
| FR | 2924331 A1 | 6/2009 |
| FR | 2979534 A1 | 3/2013 |
| JP | H 01275766 A | 11/1989 |
| WO | WO 94/19045 A1 | 9/1994 |
| WO | WO 96/35399 A1 | 11/1996 |
| WO | WO 02/066693 A1 | 8/2002 |
| WO | WO 02/083031 A2 | 10/2002 |
| WO | WO 2004/060438 A2 | 7/2004 |
| WO | WO 2005/097001 A1 | 10/2005 |
| WO | WO 2005/102458 A2 | 11/2005 |
| WO | WO 2007/034077 A1 | 3/2007 |
| WO | WO 2007/048935 A2 | 5/2007 |
| WO | WO 2007/051177 A2 | 5/2007 |
| WO | WO 2009/098408 A2 | 8/2009 |
| WO | WO 2011/051177 A1 | 5/2011 |
| WO | WO 2013/034858 A1 | 3/2013 |
| WO | WO 2013/079362 A2 | 6/2013 |

OTHER PUBLICATIONS

International search report dated Dec. 17, 2012 for PCT/FR2012/051996.
Office action dated Nov. 24, 2015 for U.S. Appl. No. 14/343,321.
U.S. Appl. No. 14/646,356, filed May 20, 2015, Perrin.
Office action dated Jun. 16, 2015 for U.S. Appl. No. 14/343,321.

* cited by examiner

A.

B.

MEDICAL DEVICE FOR SUPPORTING AN IMPLANT OR PROSTHESIS

The present invention describes a novel medical device for supporting an implant or prosthesis. Said device is made of a rigid or semi-rigid material and receives an implant or a prosthesis in a removable manner. It remains in place as long as the patient suffers no harm associated with this implantation, and the implant or the prosthesis is renewed surgically or endoscopically, in particular by the oral route, as many times as is necessary. Said device is composed of two parts, one of which constitutes an upper ring, and the other of which constitutes a lower ring, and it is intended to receive an implant or a removable prosthesis at the upper ring and to be installed in situ by means of the lower ring.

Implants and prostheses are generally inserted surgically and are replaced when the materials from which they are made degrade, or when they are obstructed or rendered non-functional by organic or cellular materials. In brief, if replacement is technically possible, and if the state of health of the patient so permits, the surgeon will implant a new functional medical device to replace an identical but defective medical device. This has the disadvantage of causing trauma to the implantation site, in the sense that the tissue which has formed around and on top of the implant or the prosthesis will be damaged during the replacement.

The present invention proposes an alternative that is less traumatic to the patient, since the medical device for supporting an implant or prosthesis according to the invention can be colonized by or integrated with the surrounding cells and remains in situ when the surgeon replaces the implant or the prosthesis. The environment, in particular the cellular environment, is therefore not damaged at all by this surgical procedure. The patient recovers more quickly from this procedure for replacement of the implant or prosthesis, and the surgeon does not have to perform any fixing procedure, since it is the novel device itself that ensures the placement, guiding and hold of the implant or of the prosthesis.

U.S. 2008/072912 describes a device for treating sleep apnea by way of a tracheotomy orifice. The aim of this device is to regulate the intra-tracheal pressure in relation to the ambient pressure under given conditions in patients who cannot be treated by the conventional nasal cannulas. Said document describes a telescopic device intended to pass through the skin and the tracheal wall of the patient. The various elements are assembled with the aid of screw threads, for example. In particular, the elements (34) and ( ) of the device (10) in FIG. 8 are not connected to each other. This device thus comprises several independent parts, in contrast to the device according to the invention.

WO 2007/048935 describes a method for producing a metal implant with open pores for tissue support and/or replacement. Said document describes in particular the production of an element made of porous titanium intended to be colonized in its anatomical zone of implantation.

WO 2011/051177 describes a tool (106) for facilitating the insertion of a speech valve (10) with a flexible retention shoulder (56) into a fistula between the trachea and the esophagus of a human patient, having a wall (108) curved to define a passage (116) with first and second open passage ends and an axis extending between the two, said wall (108) having an external surface (118) insertable into a fistula between said trachea and esophagus and defining a slot (110) which extends from the passage (116) to the external surface (118) of the wall (108), said slot (110) having an opening at the first passage end extending from the first passage end at least a part of the way to the second passage end, and at least a portion of said slot (110) progresses angularly around said axis as it progresses from the first passage end to the second passage end.

EP 1 736 119 describes a voice prosthesis device (20) for insertion into a tracheo-esophageal opening of a patient, the voice prosthesis device (20) creating a passage (36) through same, a tracheal flange (24) adjacent to a tracheal end, and an esophageal flange (26) adjacent to an esophageal end, the tracheal flange (24) and esophageal flange (26) helping to retain the voice prosthesis device (20) in the tracheo-esophageal opening, characterized in that the passage (36) comprises a first stop (44) extending inwardly from a side wall (38) of passage (36) between the tracheal and esophageal ends (24, 26), and a plurality of second stops (46) extending inwardly from the side wall (40) of the passage (36), and a valve mechanism (50) arranged in said passage and held in place by said first and second stops.

The present invention describes a medical device for supporting an implant or prosthesis, which device is composed of two parts, one of which constitutes an upper ring made of a rigid or semi-rigid, solid biocompatible material, and the other of which constitutes a lower ring made of a rigid or semi-rigid, porous or integratable biocompatible material, said device being intended to receive an implant or a removable prosthesis at the upper ring and to be installed in situ by means of the lower ring. Thus, in the device according to the invention, the technical function of the upper ring is to receive the removable prosthesis, while the technical function of the lower ring is to be integrated in situ in the patient in order to permit a cell colonization that leads to the anchoring of the device according to the invention in the tissues of the patient. It is therefore clear that the two parts are rigidly joined (connected to each other) in the device according to the invention.

The attached figures illustrate the present invention and some of the embodiments thereof. The technical features shown in the figures are not to be regarded in any way as limiting the scope of the present invention.

Figure 5:
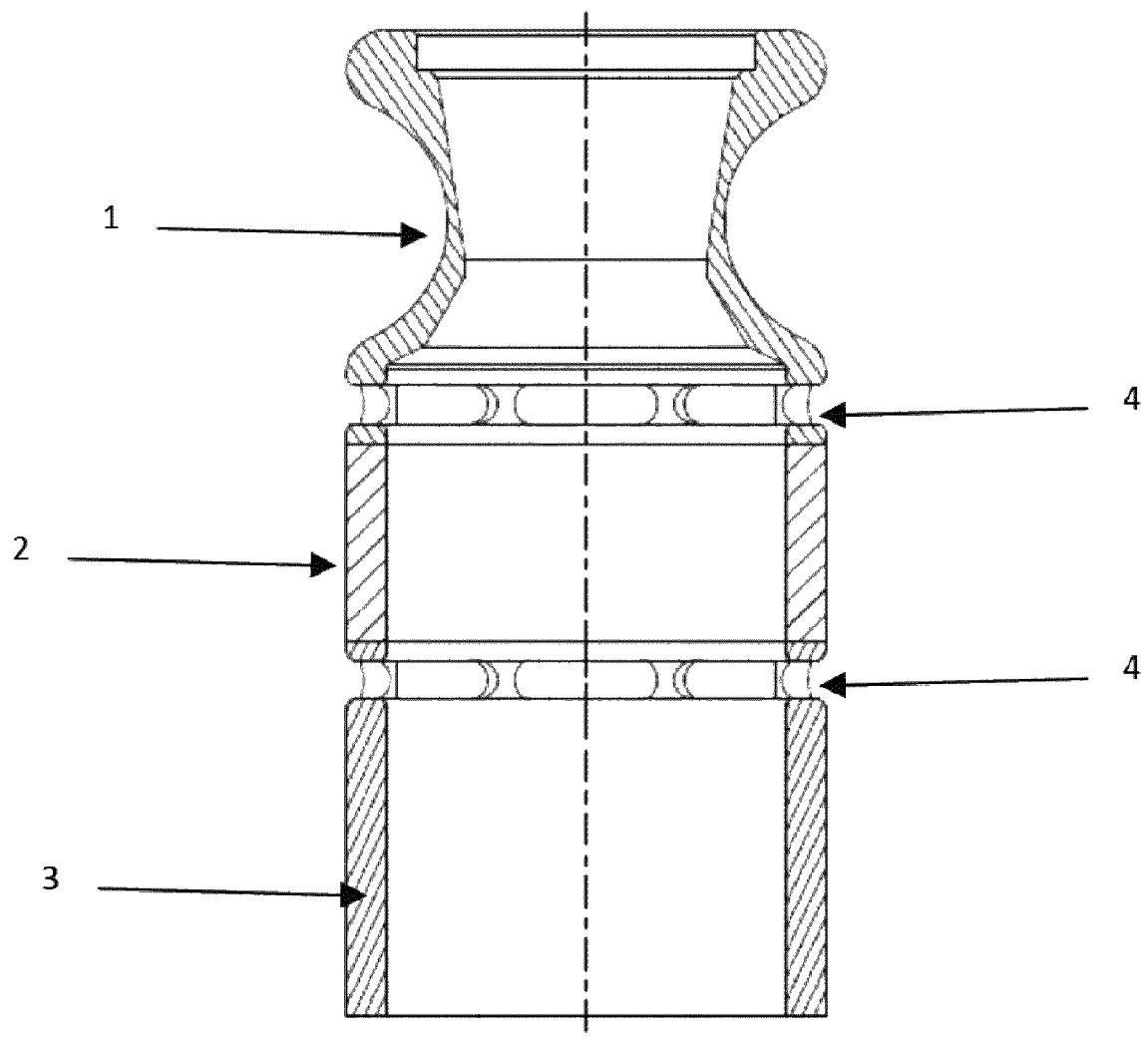

FIG. 5 shows a particular embodiment of the medical device according to the invention in which an element (3) is added under the lower ring (2). This typically represents a support for a laryngeal implant which will be fixed on the trachea after laryngectomy. The areas with openings (4) permit fixation to the surrounding tissues by suturing.

Figure 6:
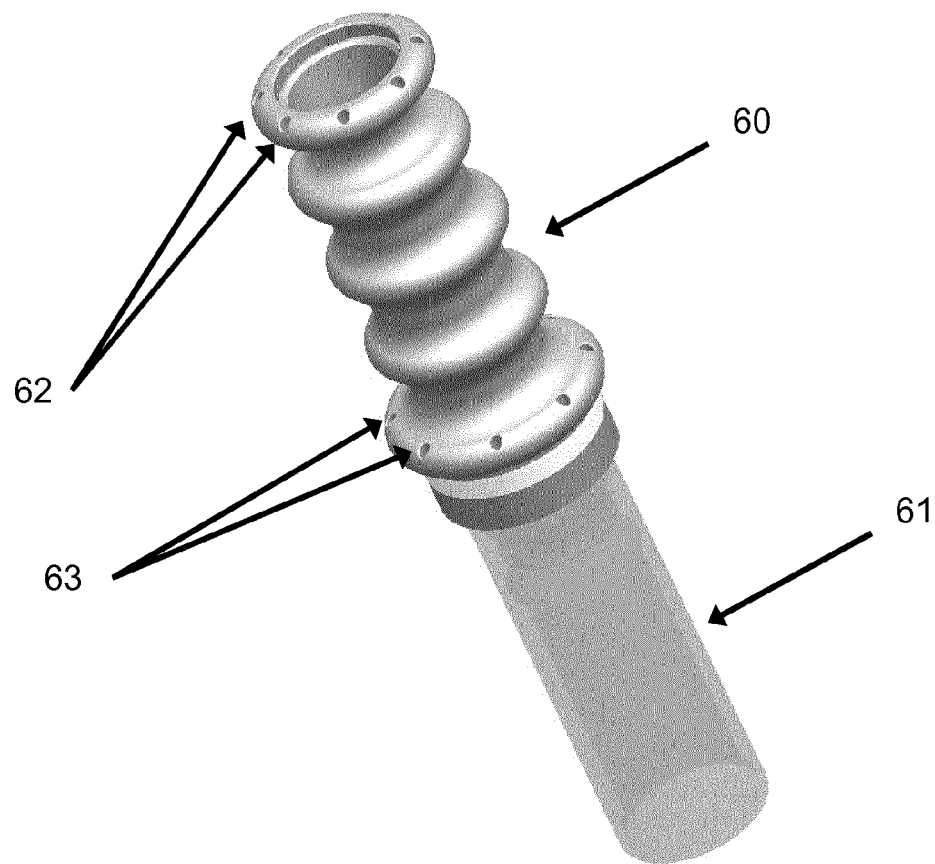

FIG. 6 shows a device (60) according to the invention, which represents a support for a laryngeal prosthesis. This device (60) has a grooved shape, and a tube (61) has been inserted into this device. The orifices (62) and (62) allowing the passage of sutures for implantation of the device are also visible.

Figure 7:
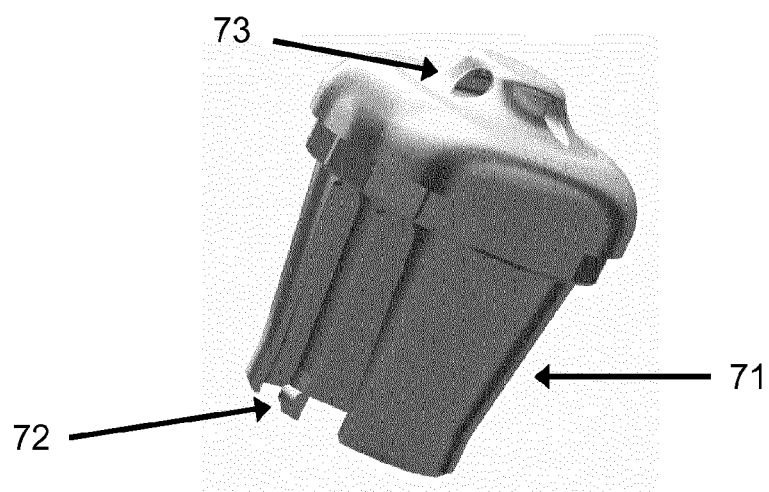

FIG. 7 shows a stopper (71) intended to be fixed in the upper part of the device (60), in order to close the latter. An anchoring means (72) has been shown, and also orifices (73)

intended to allow threads to be passed through in order to withdraw this stopper (71) for insertion of a laryngeal prosthesis.

Figure 8:
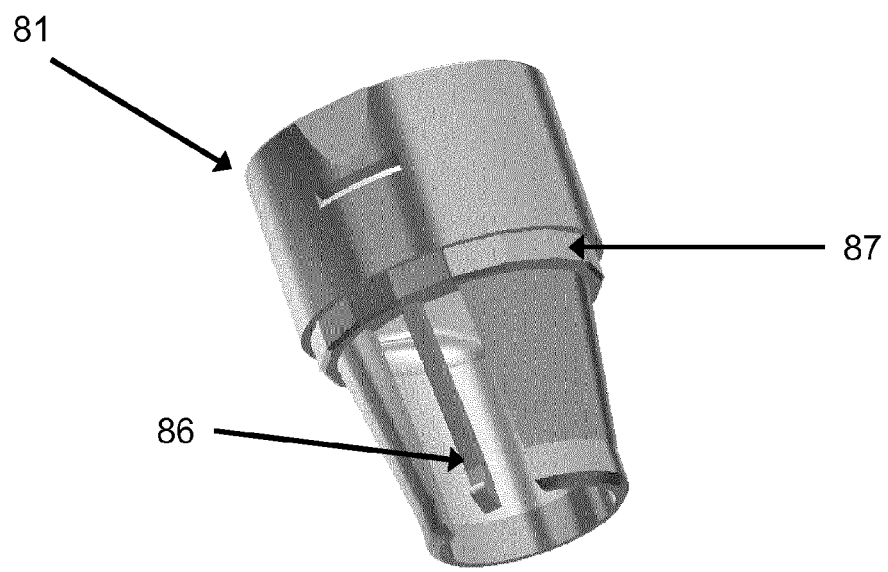
Figure 8:
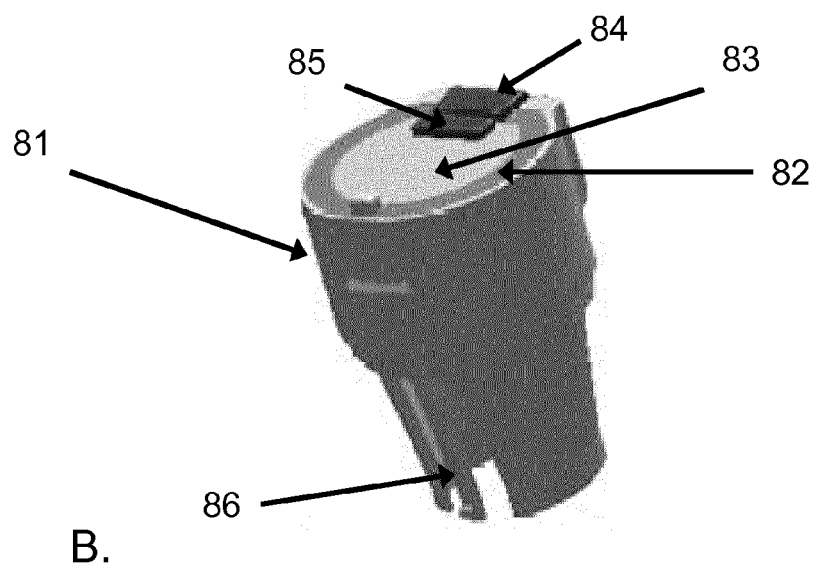

FIG. 8 shows a laryngeal prosthesis (81) which is intended to be inserted into the device (60) and which has the elements needed to obtain a function similar to the natural larynx. Two flaps (82, 83) can thus be seen, and also two hinges (84, 85). The element (86) permits anchoring of the prosthesis (81) in the ring (60), preventing any movement in translation. The elements (87) permit suitable positioning of the prosthesis (81) in the ring (60) when the latter has facets in its upper part. These elements also prevent the prosthesis (81) from moving in rotation in the ring (60).

Figure 9:
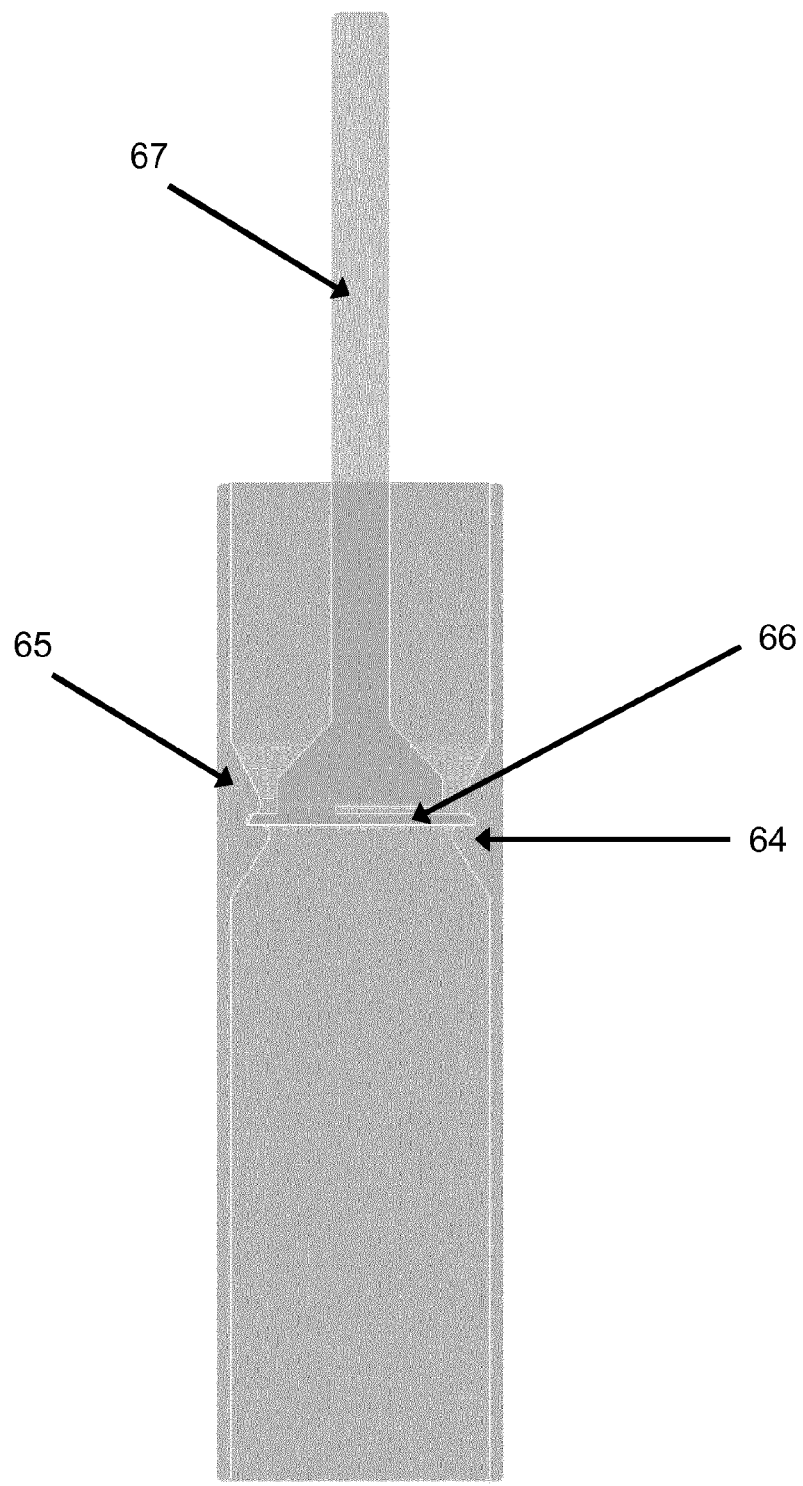

FIG. 9 shows a cross section of the tube (61) shown in FIG. 6. The stopper (66) will be seen in particular, and also its tab (67), which is provided for withdrawing it through the mouth. Elevations (64, 65) defining a neck permit fixation of the stopper (66) and prevent any accidental movement in translation in the tube (61).

Figure 10:
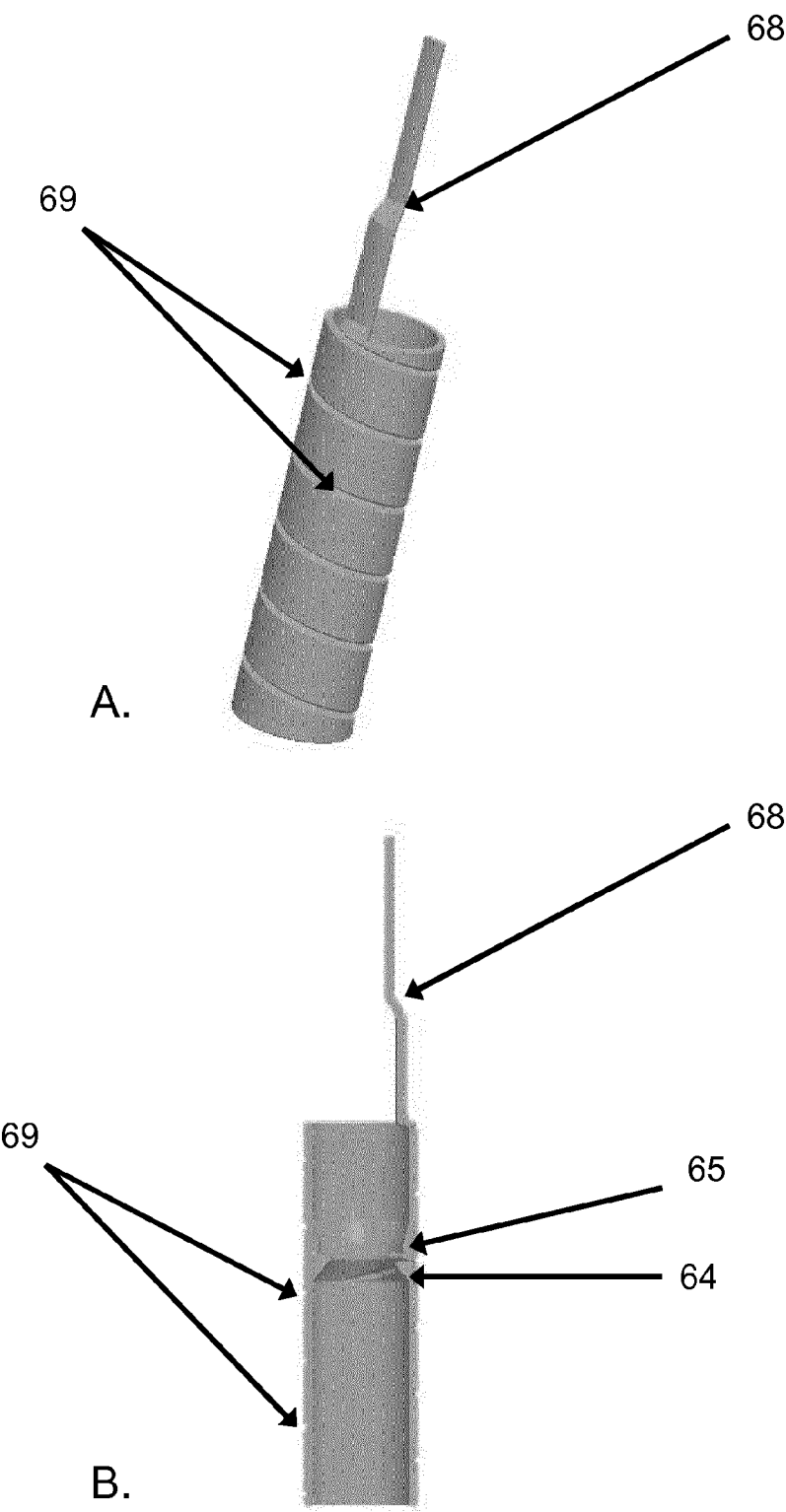

FIG. 10 shows another embodiment of the tube (61). A groove (69) is shown which allows the tube to be torn along this groove after pulling on the tab (68). In FIG. 10.B, which shows this tube (61) in cross section, the elevations (64, 65) permitting the fixation of the stopper can also be seen. In this embodiment, the tube (61) can be withdrawn through the mouth.

The present invention more particularly describes a medical device for supporting an implant or prosthesis, characterized in that it is composed of two parts, one of which constitutes an upper ring (1) made of a rigid or semi-rigid, solid biocompatible material, and the other of which constitutes a lower ring (2) made of a rigid or semi-rigid, porous or integratable biocompatible material, said device being intended to receive an implant or a removable prosthesis at the upper ring (1) and to be installed in situ by means of the lower ring (2).

The upper (1) and lower (2) rings are made of a rigid or semi-rigid biocompatible material such as ceramics, metals or metal-based alloys, polymers such as silicone, or materials of natural origin. In a particular embodiment, the biocompatible material is rigid and of a metallic nature. In a preferred embodiment, the upper (1) and lower (2) rings are made of a biocompatible material of a metallic nature, preferably titanium or a titanium-based alloy. In another preferred embodiment, the upper ring (1) is made of solid titanium or of an alloy based on solid titanium, and the lower ring (2) is made of porous titanium or of an alloy based on porous titanium.

Figure 3:
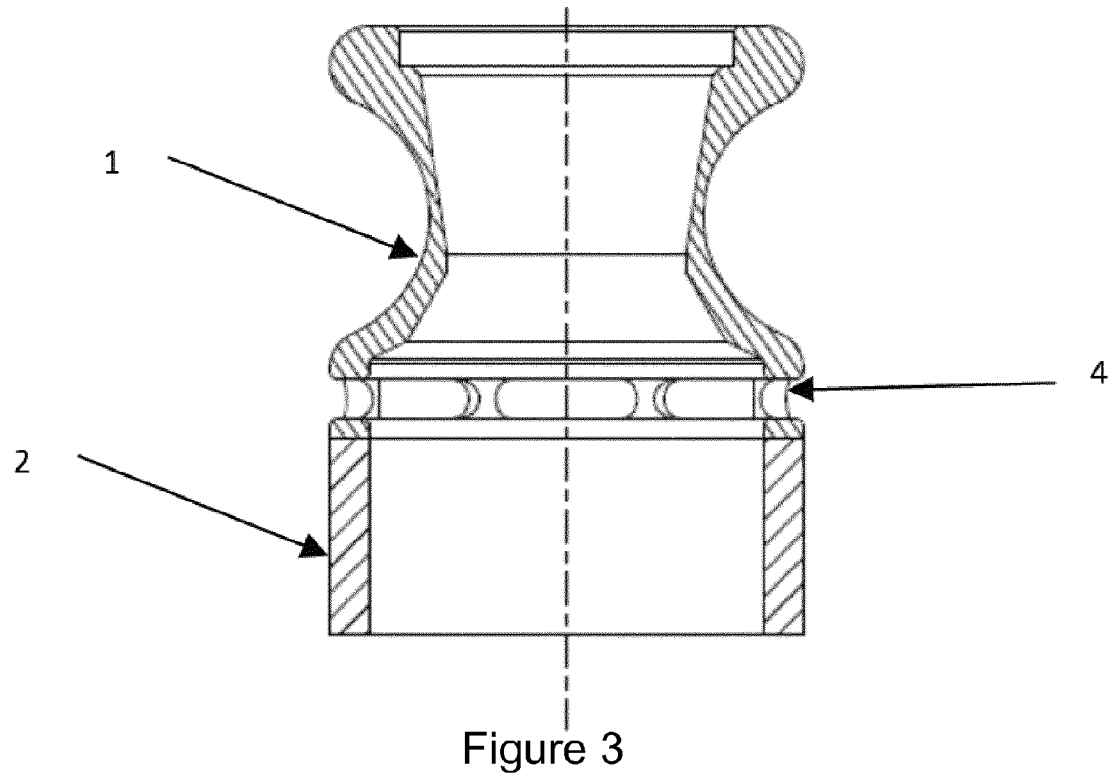
FIG. 3 shows a complete medical support device according to the invention. The upper ring (1) and the lower ring (2) can be seen here.

The shape of the upper ring is chosen depending on the implant or the prosthesis that it will receive. This shape, and the material chosen, will allow the implant or the prosthesis to be fixed directly to the medical support device according to the invention. Thus, the shape of the upper ring (1) is selected in order to receive the shape of the implant or of the prosthesis for which it will provide the support, and said upper ring (1) can be equipped with a means for anchoring the implant or the prosthesis. Said anchoring means is selected from among a fixation system providing locking by rotation, by shrink-fit or force-fit assembly, by threading, by fixing with springs (clips), by lugs, by hoops, by countersinking or by interlocking. In a preferred embodiment, the anchoring means is a system of clipping or fixing with springs. Ideally, the upper ring (1) has a concave outer geometry, allowing the total mass of the component to be reduced, while at the same time ensuring that it does not injure the patient. In a particular embodiment, the upper ring (1) has an outer shape that is cylindrical, then concave, and once again cylindrical in its area of contact with the lower ring (2). This is illustrated by FIG. 3. This upper ring (1) can also be provided with facets in its upper part, by which the implant or the prosthesis to be inserted can be locked in rotation. FIG. 8.A shows, in a laryngeal prosthesis, the elements (87) complementing the facets that may be present in the upper ring (1). This allows the implant or the prosthesis to be placed in the ring in the position desired by the surgeon, if this implant or prosthesis is not a body of revolution. The number of possible positions for the implant or the prosthesis depends on the number of facets in the upper ring (1). Generally, it is preferable to have between 12 and 20 facets, in particular 16 facets, which allows this implant or prosthesis to be turned in steps of 18 to 30 degrees (in particular 22.5 degrees). Any other equivalent means may be considered.

The device according to the invention is in fact preferably symmetrical about an axis of revolution, which allows the surgeon to implant it without worrying about a given orientation of this device, since the correct orientation of the implant or of the prosthesis is obtained by virtue of the presence of the facets at the place where this implant or prosthesis is to be inserted into the device.

In a particular embodiment of the medical device according to the invention for supporting an implant or prosthesis, the lower ring (2) and the upper ring (1) have openings (4) that allow the device to be sutured to the surrounding tissues by surgery.

In another embodiment, the medical device according to the invention for supporting an implant or prosthesis also has an element (3) situated under the lower ring (2) and made of a rigid or semi-rigid biocompatible material, said element (3) contributing to holding the device according to the invention in position. In this case, the medical device according to the invention for supporting an implant or prosthesis has three parts, one of which constitutes an upper ring (1) made of a rigid or semi-rigid, solid biocompatible material, the other of which constitutes a lower ring (2) made of a rigid or semi-rigid, porous or integratable biocompatible material, and the third of which constitutes an element (3) made of a rigid or semi-rigid biocompatible material, said device being intended to receive an implant or a removable prosthesis at the upper ring (1) and to be installed in situ by means of the lower ring (2). Such a device is illustrated in FIG. 5.

The upper ring (1) and the element (3) can additionally be provided with openings (4) intended to receive surgical sutures by which the surgeon will fix the device definitively to the implantation tissue. The implant or removable prosthesis will be engaged on the upper ring (1) by way of an anchoring means. The sutures will block the device according to the invention on the implantation tissue, while the removable part (implant or prosthesis) is fixed by an anchoring means as described above and not by surgical sutures.

The medical device according to the invention for supporting an implant or prosthesis has a lower ring (2) whose shape corresponds to the anatomical shape of the tissue for implantation of said device. In other words, if the device according to the invention is to be fixed on tissue of a circular shape, the lower ring (2) will have a circular shape complementing the shape of said tissue, and, if the tissue has an oblong shape, the lower ring (2) will have an oblong shape complementing the shape of said tissue. Similarly, in the case where an element (3) is present under the lower ring of the device according to the invention, the shape of the lower ring (2) and of the element (3) corresponds to the anatomical shape of the tissue for implantation of said device. In other words, if the device according to the invention is to be fixed on tissue of a circular shape, the lower ring (2) and the element (3) will both have a circular shape complementing the shape of said tissue.

The lower ring (2) is intended to be colonized by or integrated with the implantation tissue, and it is therefore made of a semi-rigid or rigid, porous or integratable biocompatible material. Such a material is typically solid metal or an alloy based on solid metal, porous metal or an alloy based on porous metal, silicone or ceramic, these elements being used alone or in combination, and in various forms such as a solid ring, a superposition of layers, a thread, a lattice, a weave, a bond, a stent or spring, or any other equivalent form satisfying the technical features of the present invention.

The element (3), which is fixed to the lower ring (2), is composed of a rigid or semi-rigid material that is biocompatible. The element (3) can be a third ring made of a metal or of a metal alloy, preferably titanium. The element (3) can also be a ring made of ceramic or silicone. The element (3) can finally be a thread, a lattice, a weave, a bond or a stent, also made of a metal or non-metal biocompatible material. In a particular embodiment, the element (3) is fitted on the lower ring (2) and matches the shape thereof. Its role is to stabilize the device according to the invention.

The novel medical support device according to the invention is particularly suitable for supporting a laryngeal implant. Some diseases such as cancer sometimes result in total ablation of the larynx. Each year, about 1,850 people in France undergo a total laryngectomy. To restore the functions of the larynx, several techniques have been proposed, such as tracheostomy or a laryngeal transplant. However, tracheostomy often leads to isolation associated with loss of speech, and a total laryngeal transplant is out of the question in the case of patients treated for cancer. Consequently, the present invention describes a medical device for supporting an implant or prosthesis, which device is implanted on the trachea of a patient having undergone total ablation of the larynx and which thus ensures a stable join between said trachea and the implant or the laryngeal prosthesis. In a preferred embodiment, the above-described medical device for supporting an implant or prosthesis is one in which the upper ring (1) and the element (3) are made of solid titanium or of an alloy based on solid titanium, and the lower ring (2) is made of porous titanium or of an alloy based on porous titanium, and, moreover, the upper ring (1) and the element (3) are equipped with openings (4) to permit fixation by suturing to the tissues of the trachea.

Following the implantation of the support according to the present invention and of a laryngeal prosthesis or implant according to the prior art, the functions of the trachea and in particular of the larynx are thereby restored. Laryngeal prostheses such as those described in the patent EP 2 240 120 or in the French application FR1211841 are particularly suitable for fixing to the support device according to the invention. In the case of the intralaryngeal prosthesis described in the application FR1211841, both the prosthesis and the support according to the present invention are made of a rigid or semi-rigid biocompatible material, preferably a metal, more preferably titanium. The prosthesis described in the application FR1211841 has a device with flaps, and a skirt or flange for keeping it in position in situ. In the case where said prosthesis is used on the support described in the present invention, this device with flaps does not have a flange, since the latter is no longer of any use in the case of fixation to a support according to the invention. In this case, the solid parts are made of solid titanium, and the porous parts are made of microporous titanium. The microporous titanium can be obtained in particular by the method described in EP 1 940 480. The intralaryngeal prosthesis described in EP 240 120 is made of a semi-rigid material and is equipped with a support means forming a flange. For the same reasons as those mentioned above, this flange is of no use if the intralaryngeal prosthesis is mounted on a support such as the one described in the present invention. In this case, the intralaryngeal prosthesis is made of a semi-rigid material such as silicone, and the support according to the invention is made of a rigid or semi-rigid material, preferably a metal.

In a preferred embodiment, the medical device according to the invention for supporting an implant or prosthesis is characterized in that it comprises an upper ring (1) made of solid titanium or of an alloy based on solid titanium, a lower ring (2) made of microporous titanium or of an alloy based on microporous titanium, and a support element (3) made of a rigid or semi-rigid biocompatible material such as solid metal, porous metal, silicone, ceramic, alone or in combination, in various forms such as a solid ring, a superposition of layers, a thread, a lattice, a weave, a stent, or any other equivalent form satisfying the technical features of the present invention.

In a particular embodiment, the support according to the invention will have all the technical features described above, and also several openings separating the rings (1) and (2) and separating the ring (2) and the element (3), such that the surgeon can fix the device to the surrounding tissues.

In a particular embodiment, the invention relates to a kit comprising an above-described medical device and also a tube (61) whose external diameter is such that it can be inserted into the lower part of said device (part made of porous metal), in such a way that this insertion permits good sealing. Such a device (60) joined to the tube (61) is shown in FIG. 6.

In a particular embodiment, said device is intended to be positioned in proximity to the trachea of a patient. Consequently, the length of the tube (61) is between 3 and 9 cm, preferably about 7 cm. In any case, the surgeon will be able to cut the tube to the desired length, taking into account the anatomy of the patient (size of the neck, site of the tracheostomy hole, size of the tissues removed during the operation, etc.), it being understood that this tube should be able to serve as a prop in order to allow the device to be correctly positioned with respect to the trachea. In particular, the tube can be inserted into the trachea to ensure that the alignment is suitable. The tube as such is also part of the subject matter of the invention.

In this embodiment, said device is preferably made of titanium. In this application, it will also be able to be designated as a tracheal ring.

In a preferred embodiment, the tube (61) is a silicone tube. Any other material can be used, although it should be borne in mind that this material must nonetheless have the following properties: a degree of deformability (since this tube must be able to be inserted into the top of the trachea of the patient), a degree of rigidity (since this tube must be able to serve as a prop to ensure that the device is correctly positioned in the axis of the trachea), and biocompatibility (on account of its implantation in humans).

In a particular embodiment (and subject to the presence of elevations such as those described below), the thickness of the tube (61) is constant along its entire length. In particular, a tube is envisioned with an external diameter of 20.5 mm and an internal diameter of 18 mm (i.e. a thickness of the tube of 1.25 mm).

In another embodiment, said tube (61) has a helically configured tear zone (helical groove) (69), which allows the tube (61) to be torn after traction is applied to one of the ends of the tube (61). This is illustrated in FIG. 10. In this embodiment, the thickness of the tear zone must make it possible to maintain the integrity of the tube in vivo, while permitting controlled tearing under the effect of the traction. A thickness of this zone of the order of about 0.05 mm is envisioned. In this embodiment, it is preferable that the tube has, at one of its ends (the end that will be introduced into the tracheal ring), a rod/tab (68) that it will be possible for the surgeon to grip (with the aid of forceps) in order to exert the traction allowing the tube to be torn. This embodiment makes it possible to withdraw this tube (61) through the mouth when it is no longer of use, after evaluation by the surgeon. Such a tube can be obtained in a suitable mold.

The kit can also comprise a stopper (66) (as with the tube (61), this stopper (66) is preferably made of silicone). This stopper (66) is removable and is intended to be positioned in the tube (61). It is intended in particular to prevent mucus from rising from the lungs and contaminating the tracheal ring during the colonization, in particular by limiting the presence of bacteria during this colonization.

In this embodiment, the tube (61) preferably has two elevations (which between them define a neck) in its internal diameter (one being higher than the other). This allows the stopper to be clipped in place, such that it does not move after implantation. The higher elevation (64) is situated in the lower part of the tube (61) (distally from the tracheal ring) and serves to prevent the stopper from dropping into the trachea. The less high elevation (65) is situated in the proximal part of the tracheal ring.

The diameter of the stopper (66) is therefore less than the internal diameter of the tube (61). In a particular embodiment, the stopper (66) has a tab (67). This tab is intended to allow the stopper (66) to be easily withdrawn before the prosthesis (81) is fitted. It suffices in fact to pull on this tab in order to release the stopper (66) and withdraw it through the mouth. This tab is therefore sufficiently long and penetrates into the tracheal ring after the tube (61) has been fixed there.

In this embodiment, the tracheal ring is positioned in the patient just after the ablation of the larynx, during the same operation. The tube (61) is intended to be introduced into the trachea of the patient and to position the tracheal ring in such a way that the latter is correctly aligned with the trachea. The presence of this tube (61) can also serve as a prop for the cells that colonize the area of implantation of the device, allowing these cells to form a conduit around this tube (61) and ensuring that they do not migrate underneath or inside the tracheal ring, which could reduce the useful diameter of the trachea or even occlude it. Finally, it makes it possible (particularly in the presence of the stopper (66)) to protect the cells, which are intended to colonize the area of porous titanium, from the presence of mucus coming from the lungs. This is intended to maintain a colonization environment that is as sterile as possible. This tube (61) will be able to be withdrawn by the surgeon after a certain time (once he considers the tracheal ring to be suitably fixed).

In this embodiment, the kit can also comprise a stopper (71) intended to be introduced into the upper part (part made of rigid metal) of the tracheal ring (60), in order to obstruct it and to guarantee that it is sealed, and to avoid any passage of air or of food during the phases of colonization and cicatrization. On its lower part, this stopper can comprise elements (72) permitting reversible fixing to the tracheal ring via the anchoring means of the tracheal ring, if the latter has such means. It can comprise orifices (73) in its upper part in order to allow one or more threads to be passed through so as to withdraw said stopper through the mouth after cicatrization and implantation of the ring in the patient.

The stopper can have a male cone shape which will fit into the tracheal ring (upper part possibly having a female cone shape). It will of course have the elements allowing it to be engaged in the facets of the tracheal ring, if the latter has such facets.

The kit according to the invention can also contain a removable element (larynx prosthesis) intended to be fixed on the device according to the invention after implantation in the patient. Such an element, also forming part of the subject matter of the invention, is shown in FIG. 8.

This removable element is composed of a body (81) made of biocompatible metal (preferably of solid titanium).

In the upper part of the removable part (which will be situated proximal to the end of the tongue), there are two concentric flaps (82, 83). Downward opening of the small flap (83) permits inhalation, while upward opening of both flaps (small+large) permits exhalation.

The principle of the flaps is described in the application EP 2 240 120. However, the removable element as envisioned for implementation of the present invention also has means allowing it to be anchored to the device as described above, so as to be joined to the latter after implantation in situ.

Thus, the removable laryngeal prosthesis has a distal portion (81) forming an annular supporting framework (of which part is intended to be fixed to the device (tracheal ring) according to the invention), and a central portion forming an obturator intended to allow air to pass through and to prevent the passage of any other element. In a preferred embodiment, said obturator comprises i) a peripheral part forming a first flap (82) rigidly connected to the annular supporting framework at a first hinge region (84), said first flap (82) being able to lift under the effect of the overpressure resulting from the exhalation by the patient, and ii) a central part forming a second flap (83) connected rigidly to the first flap (82) at a second hinge region (85), said second flap being able not only to lower, under the effect of the partial vacuum exerted by the air inhaled by the patient, but also to cooperate with the first flap in order to lift following the exhalation by the patient, said first and second flaps cooperating with each other in a totally hermetic manner.

To be able to ensure the movement of the one or more flaps while at the same time maintaining perfect leaktightness, the hinges (84) and (85) are preferably made of a semi-rigid or else rigid material. It is expedient that the movement is made possible with a low respiratory pressure, but also that the hinges allow the flaps to resist the pressure of the food bolus or of any fluid that bears on the obturator with a greater or lesser force. Moreover, it is necessary that the hinges resist colonization and ensure a regular and lasting movement of the flaps. Moreover, the hinge area must ensure perfect stability of the axes of rotation with respect to the supporting framework of the device, in order to guarantee the leaktightness upon closure.

In the preferred embodiment, a semi-rigid (or super-elastic) material is understood as a material that is sufficiently flexible to be able to ensure a certain degree of elasticity, while at the same time being rigid enough to be able to resist a low pressure and retain its shape. Such a semi-rigid material can be chosen from among plastic, gum, a resin or else silicone. A super-elastic material such as Nitinol can also be used. A preferred material is silicone, in particular silicone 70 Shore A. The hinge is then composed of a tab made of silicone, fixed to the outer part of the annular support framework by way of two stubs and a plate made of solid titanium. The other end of the semi-rigid tab is fixed on the flaps (82) and (83) by any suitable means. Particular mention is made of a perforation of a small part of the flap, creating orifices through which the semi-rigid material will be poured. This mechanism has the advantage of being perfectly functional and biocompatible.

In another embodiment, the hinge is made of a rigid material. Rigid material is understood as a mechanism such as a mechanical hinge composed of a rigid shaft which engages in a cutout formed in the flaps (82) and (83). The rigid shaft can be made of ruby or of a metal such as titanium or a titanium-based alloy or any other rigid biocompatible metal. More generally, it is possible to use all the mechanisms used in watch-making and made from biocompatible materials. This mechanism has the advantage of being robust, since it is made of rigid and biocompatible materials that do not degrade or that do so only slightly.

In a preferred embodiment, the laryngeal prosthesis intended to be inserted into the tracheal ring also has an assistance device placed on the annular supporting framework (81) and/or the first flap (82). This assistance device can be mechanical, electrical or electronic.

In a preferred embodiment, the assistance device is a magnetized device. Magnetized device or magnetized element is understood as one or more permanent magnets of the lanthanide type which are biocompatible or are rendered biocompatible by various treatments known to a person skilled in the art, or else are enclosed hermetically in a suitable housing provided for this purpose. Said magnetized device can be placed either on the first flap (82) or on the internal surface of the supporting framework (81). When the first flap is in the closed position, a metallic element is placed opposite the one or more magnets. Metallic element is understood as one or more metallic elements capable of being magnetized and placed in such a way as to come into contact with the one or more magnets when the first flap is in the closed position. The nature of the magnetized device will be able to be adapted to each situation by varying the number of magnets and/or their position, for example. It is also conceivable to use two magnets facing each other.

Thus, in a particular embodiment, the laryngeal prosthesis has an assistance device consisting of a metallic element arranged in the area of the annular supporting framework (81) and coming into contact with a magnetized element arranged in the area of the first flap (82). In a preferred embodiment, the laryngeal prosthesis has an assistance device consisting of a metallic element arranged in the area of the first flap (82) and coming into contact with a magnetized element arranged in the area of the annular supporting framework (81).

A mechanical assistance device can also be positioned on each of the flaps in order to facilitate their cooperation in the desired function. According to this embodiment, the laryngeal prosthesis is such that the first flap (82) and the second flap (83) comprise an assistance device so as to permit the lifting only of the second flap (83) and the simultaneous lowering of the first flap (82) and of the second flap (83). In a preferred embodiment, the flaps (82, 83) of the device according to the invention comprise an assistance device so as to permit the lowering only of the second flap (83) and the simultaneous lifting of the first flap (82) and of the second flap (83).

When said device itself has anchoring means, said removable element has means complementing those (86). In a particular embodiment, the part of said removable element intended to be introduced into or attached to the device according to the invention is asymmetrical. This assists the surgeon during the implantation of this removable element by indicating the correct orientation that has to be observed. Thus, the laryngeal prosthesis is positioned in such a way that the hinge part (84) is applied against the base of the patient's tongue. This positioning and this orientation can be obtained by slightly pivoting the laryngeal prosthesis according to the facets of the tracheal ring, if the latter has these, until the suitable position is reached.

The present invention also describes a method for supporting and fixing an implant or a prosthesis according to the present invention, in which method a device according to the invention is placed securely on a tissue intended to receive an implant or a prosthesis. The method involves surgically fixing the support according to the invention on a tissue intended to receive an implant or a prosthesis.

In a particular embodiment, the invention relates to a method for supporting and fixing an implant or a prosthesis according to the present invention, in which method said support is placed securely on the trachea of a patient in order to receive a laryngeal implant or prosthesis. The method involves a step of surgically fixing the support to the walls of the trachea of the patient who has undergone a laryngectomy. Once the support is fixed to the trachea, the implant or the prosthesis is inserted through the mouth and clipped onto the support.

Thus, the invention also relates to a method of treating a patient having undergone ablation of the larynx, comprising the step of introducing a laryngeal prosthesis into this patient, said prosthesis being introduced through the mouth of the patient.

In particular, the invention relates to a method comprising the step of introducing a laryngeal prosthesis orally into a patient having undergone a laryngectomy, and of fitting a device as described above, said laryngeal prosthesis being fixed to said device.

The invention relates to a method of treating a patient having to undergo a laryngectomy, said method comprising the steps of a) ablation of the larynx, b) fitting a device as described above in the trachea of the patient.

In this method, said device is sutured to the tissues of said patient. In particular, said device is preferably positioned in such a way that the part made of solid titanium is sutured to the hyoid bone and/or to the base of the tongue, while the part made of porous titanium is positioned end to end with the upper part of the trachea and connected thereto by loose sutures. It is thus placed slightly (0 to 3 mm) above the trachea of the patient.

In this embodiment, it is preferred to use a tube (preferably made of silicone), of which one end is inserted into said device (from the side with the porous metal) and the other end is inserted into the trachea, by which means it is possible to guide the introduction and placement of the device during the intervention.

In this connection, the surgical steps that should be performed within the context of the present invention are the following.

Ablation of the larynx and opening of a tracheotomy hole; this tracheotomy is at present necessary to allow the patient to continue breathing during the period of colonization of the tracheal ring. The tracheotomy hole is intended to be plugged after the laryngeal prosthesis has been fitted in place.

Placement of the tracheal ring (introduction of the silicone tube into the trachea, and suturing of the tracheal ring to the tissues of the patient); the ring will be surrounded by muscles in order to permit good physiological integration and to hold it in place without movements.

This ring has a stopper in its upper part (which can be inserted after the ring has been placed in situ), which is also the rigid metal part proximal to the base of the tongue. A stopper (preferably made of silicone, because of the deformability and biocompatibility of this material) is also present in the silicone tube.

Cicatrization and colonization of the porous metal part by cells: this phase lasts 4 to 8 weeks.

Withdrawal of the metal and then the silicone stoppers (through the mouth).

If appropriate, withdrawal of the tube through the mouth or via the tracheotomy hole.

Placement of the artificial laryngeal prosthesis through the mouth.

Plugging of the tracheotomy hole.

The invention also covers a method for replacing a laryngeal prosthesis fixed on a device according to the invention, characterized in that said prosthesis is withdrawn, and a new laryngeal prosthesis is reattached to said device. The prosthesis to be replaced is withdrawn by any means (especially with the aid of forceps) from the laryngeal ring, this being done by way of the mouth. The new prosthesis is reinserted by way of the mouth and fixed to the laryngeal ring. Although the laryngeal prosthesis can withstand several million cycles of opening/closing, it may conceivably need to be replaced.

EXAMPLES

Example 1

Description of the Medical Device for Supporting an Implant or Laryngeal Prosthesis The device according to the invention has an upper ring (1), a lower ring (2) and an element (3).

Figure 1:
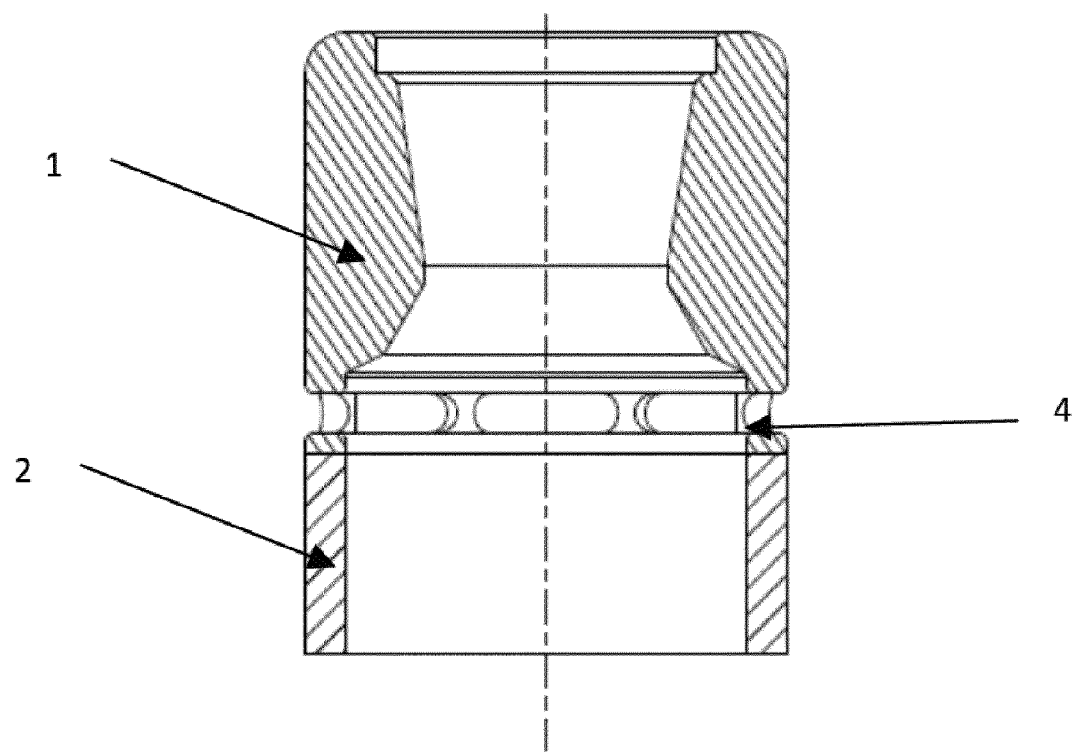
FIG. 1 shows the upper ring (1) of the medical support device according to the invention. This ring can have several shapes depending on the implant or the prosthesis that is to be received.
Figure 2:
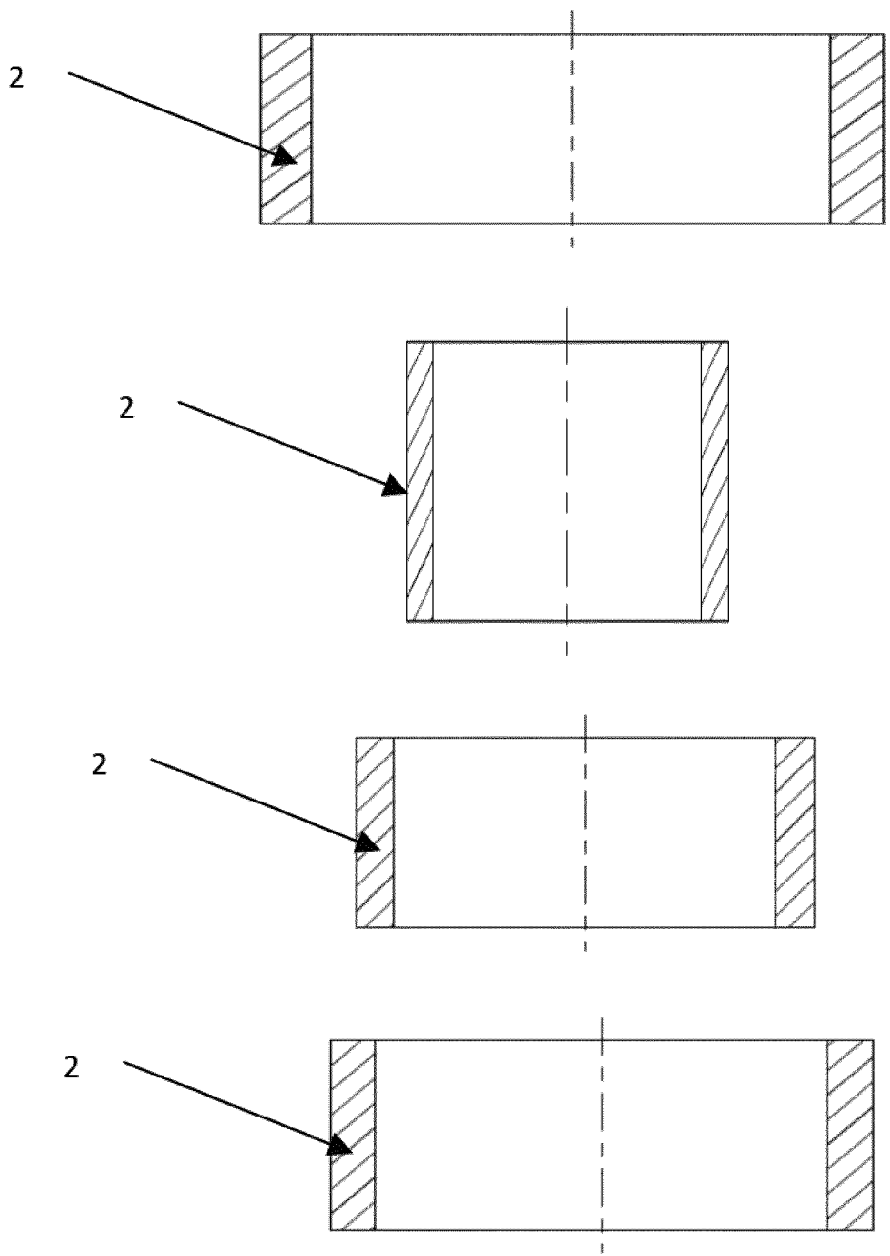
FIG. 2 shows the lower ring (2) of the medical support device according to the invention. This ring can have different lengths and thicknesses depending on the implant or the prosthesis that is to be received.

The upper ring (1) is preferably made of solid titanium. It has an anchoring system intended to receive an implant or a laryngeal prosthesis. The anchoring system can be a fixation system providing locking by rotation, by shrink-fit or force-fit assembly, by threading, by fixing with springs (clips), by lugs, by hoops, by countersinking or by interlocking. The upper ring has a shape chosen depending on the shape of the implant or of the prosthesis and of the chosen anchoring system. In the case of the support according to the invention for a laryngeal implant, this upper ring (1) is cylindrical with an outer shape that is either straight (see FIG. 1) or truncated (see FIGS. 3 to 5) at its center with cylindrical and straight ends.

In another embodiment, the upper ring has a grooved (FIG. 6) or even threaded shape. This shape is particularly advantageous in the context of a support for a laryngeal implant. In this case, the ring is surrounded by muscle (in particular the muscular flap of the major pectoral muscle or the sub-hyoid muscles) in order to maintain it in place (formation of a gangue around the prosthesis) and to permit colonization of the porous metal by the tissues. Such a grooved (or threaded) shape can limit the sliding of the muscles on the surface of the upper ring.

The implant or the prosthesis is fixed in this upper ring by way of the anchoring means. For a laryngeal implant, said implant is typically clipped onto the support.

Figure 4:
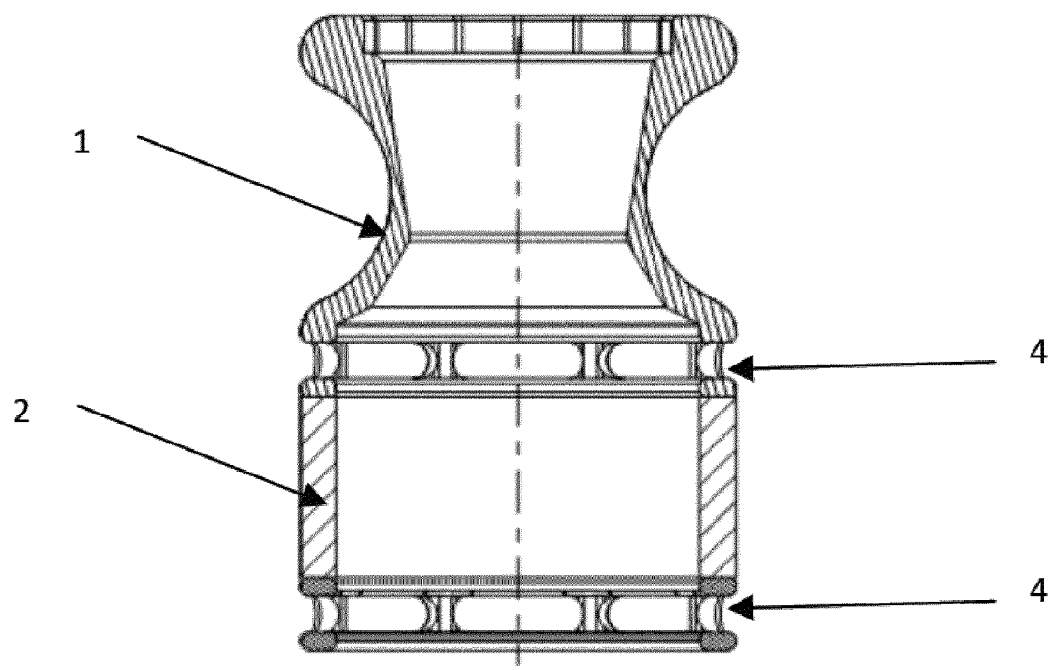
FIG. 4 shows a complete medical support device according to the invention. The upper ring (1) and the lower ring (2) can be seen here, both of them equipped with openings (4).

The lower ring (2) has a straight cylindrical shape and is preferably made of porous titanium. It is equipped with series of openings (4) so that the surgeon can sew the support onto the walls of the trachea of the patient. There can be a single series of openings between the upper ring (1) and the lower ring (2), as is illustrated in FIG. 3, but there can also be a supplementary series of openings (4) under the lower ring (2), as is illustrated in FIG. 4.

In order to stabilize the support device according to the invention on the trachea of the patient, it is also possible to provide an element (3) which will be engaged around the trachea. This element (3) is situated under the lower ring (2). The element (3) is made of a semi-rigid or rigid biocompatible material. In the case of the support for a laryngeal implant, the element (3) can be made of solid titanium.

Such a support device according to the invention for a laryngeal prosthesis is illustrated in FIG. 5. The latter shows an upper ring (1) made of solid titanium, which is welded onto a lower ring (2) made of porous titanium. The two rings are separated by an area of openings (4) that are intended to permit fixing by surgical sutures. The upper ring (1) has a cylindrical shape in its upper part, then a concave shape, and finally once again a cylindrical shape, with the same diameter as in the upper part.

The lower ring (2) has a cylindrical shape of the same diameter as the cylindrical parts of the ring (1). In its lower part, the ring (2) is equipped with an area of openings (4) that are intended to permit fixing by surgical sutures. Finally, the element (3) made of solid titanium has a cylindrical shape of the same diameter as the lower ring (2). The anchoring system is a clamp system (of the "cabletie" type, for example).

FIG. 6 also shows a view of the tracheal ring (60), with the silicone tube (61) which allows it to be positioned with precision near the trachea. This figure also shows the orifices (62) permitting suturing of the ring to the hyoid bone and/or to the base of the tongue, and also the orifices (63) permitting loose suturing to the trachea.

Properties of the Porous Titanium Used in the Production of Supports According to the Invention In the production of the support according to the invention, the preferred biocompatible metallic material is titanium or a titanium-based alloy.

The microporous titanium as described in the patents EP 1937185 and EP 1940480 is particularly suitable for the production of the lower ring (2). It is biocompatible and light in weight, and it has a porosity perfectly adapted to cell colonization.

Example 2

Surgical Method for Fitting an Artificial Larynx

The rings, prostheses have been machined and prepared by the Protip company (Strasbourg, France).

For anesthesia, the exact medication to be followed and the dosage are left to the discretion of the medical team.

The total laryngectomy is performed in accordance with the prior art. The tracheal tree is freed in order to be able to lift it some 10 to 15 mm.

A tracheostomy orifice is created lying below the proximal section approximately between the 3rd and 4th tracheal rings, with secure fixation of the margins thereof to the skin.

After removal of the larynx, the height between the hyoid bone or base of the tongue and the top of the trachea is measured in order to choose a ring whose height is the most suitable.

It is thus possible to determine the suitable size of the tracheal ring to be fitted.

| Height | Suitable ring |
|---|---|
| 45 mm < h < 60 mm | Tracheal ring 50 (mm) |
| 60 mm < h < 70 mm | Tracheal ring 65 (mm) |

The tracheal ring (60) is composed of porous titanium and of solid titanium. A silicone tube provided with a silicone stopper (61) is placed temporarily inside the titanium ring, which makes it possible to align the trachea and the ring and to strengthen the join (FIG. 6).

The stopper is made of solid titanium. Orifices (73) in the upper part allow the passage of a non-resorbable suture thread (Mersuture® 1.0) for withdrawal of the stopper during placement of the removable part (actual larynx prosthesis).

The tracheal ring is maneuvered carefully in order to avoid any injury to the patient or the user and any damage to the ring.

Before use, the state of the packaging of the ring and of the silicone tube is checked. Likewise, a check is made to ensure that the silicone stopper is rigidly connected to the silicone tube.

The integrity of the tracheal ring, of the silicone tube and of the titanium stopper (71 in FIG. 7) is also verified.

A white annular ring can be used for the manipulation of the silicone tube. It is positioned around the junction between the silicone stopper and the silicone tube during the period of the manipulation (to avoid any unclamping of the stopper during the manipulation).

The silicone tube is then inserted into the tracheal ring from the direction of the porous titanium. The white ring is withdrawn, taking care not to detach the stopper situated in the silicone tube.

The silicone tube is inserted into the top part of the trachea, the bottom of the tracheal ring (part made of porous titanium) being situated end to end with the top of the trachea (direct contact between the ring and the trachea).

The silicone tube, thus inserted into the ring and the trachea, serves as a prop (rigid join).

The top of the tracheal ring (made of solid titanium) is fixed to the hyoid bone and/or to the base of the tongue using a suture thread.

The bottom of the tracheal ring is fixed to the upper part of the trachea (ample join).

The silicone tube is fixed to the trachea with the aid of an accessible suture. In fact, it will be expedient to be able to withdraw it subsequently via the tracheotomy orifice.

A suture thread is fixed to the top of the titanium stopper, and the stopper is joined onto the tracheal ring (male cone in female cone).

The ring is then surrounded by muscle (muscle flap of the major pectoral muscle) in order to permit the colonization of the porous titanium by the tissues. If the local environment so permits, local muscles such as the sub-hyoid muscles can also be used.

The assembly composed of the prosthesis and of the muscular covering is sutured in order to form a funnel with an upper opening. The anterior wall of the pharyngeal mucosa, previously closed and sutured (using the conventional technique of closure after pharyngo-laryngectomy) is applied and sutured to the upper opening of the funnel.

Cicatrization and colonization are allowed to proceed for a period of 4 to 8 weeks before implanting the actual laryngeal prosthesis.

Implantation of the Laryngeal Prosthesis (81)

Before the operation, measures are taken to scan the anatomy in order to predict the suitable size of the removable part to be fitted (measurement of the distance between the upper part of the tracheal ring and the base of the tongue).

| Distance from the base of the tongue to the upper part of the tracheal ring | Suitable removable part |
|---|---|
| h ≤ 10 mm | Removable part 10 |
| 10 mm ≤ h ≤ 20 mm | Removable part 20 |
| 20 mm ≤ h ≤ 30 mm | Removable part 30 |

For anesthesia, the exact medication to be followed and the dosage are left to the discretion of the medical team, using the methods known in the art.

The patient is placed laying on his back. The intervention is performed by the oral route under general anesthesia.

The removable part is composed of a body made of solid titanium.

In the upper part of the removable part there are two concentric flaps. Downward opening of the small flap permits inhalation, while upward opening of both flaps (small+large) permits exhalation.

The removable part is correctly positioned when the hinge (flat part) is against the base of the tongue.

The removable part is maneuvered carefully in order to avoid any injury to the patient or the user and any damage to the removable part.

Before use, it is preferable to check the integrity of the removable part and the correct opening of the flaps. To do this, forceps or a suitable spatula are used to apply pressure to the small flap inside the prosthesis. The small flap must open without difficulty and close by itself.

The opening of the large flap is checked by opening it outward from the prosthesis. The large flap is pushed via the inside of the removable part, that is to say by introducing a stylet into the prosthesis via the lower end thereof, until an opening of approximately 45°. It should return by itself to its initial position.

In a first stage, the titanium stopper is withdrawn. If necessary, the mucosa covering the stopper is opened by laser or with the aid of micro-instruments, and the stopper is then withdrawn with the aid of forceps by which it is possible to trap the thread fixed to the upper part during placement.

By pulling on the thread, it is possible to disconnect it from the tracheal ring and remove it. This force must be exerted in the axis of the tracheal ring by holding it with the aid of forceps in order to avoid exerting traction thereon.

The silicone stopper is also removed. It is disconnected from the silicone tube and withdrawn with the aid of forceps through the ring (orally) by pulling on the tab/rod.

During this operation, the tracheal ring must also be held so as not to exert traction thereon.

With the aid of forceps, the removable part is placed on the tracheal ring until abutment (clip sensation). The removable part is correctly positioned when the flat face of the part made of titanium (where the hinge is positioned) is against the base of the tongue and the plane of the flaps is situated in the area thereof. Thus, when the large flap is opened, it touches the tongue.

Replacement of the Removable Part

The withdrawal of the removable part takes place under general anesthesia with the aid of forceps. Withdraw the assembly carefully, taking care not to exert traction on the tracheal ring.

During a change of removable part, the silicone tube can be withdrawn at any moment (as assessed by the surgeon) through the tracheotomy hole. Having withdrawn the suture of this tube to the trachea, it can be lowered in the trachea in order to recover its upper end and extract it.

The withdrawal must be carried out carefully, taking care not to exert force on the tracheal ring.

A new removable part is fitted in place using the same protocol as for the initial removable part.

The invention claimed is:

1. A medical device for supporting an implant or prosthesis, said device comprising a body including two parts, one of which constitutes an upper ring made of a rigid or semi-rigid, solid biocompatible material, and the other of which constitutes a lower ring made of a rigid or semi-rigid, porous or integratable biocompatible material, said device being intended to receive an implant or a removable prosthesis at the upper ring and to be installed in situ by means of the lower ring.

2. The medical device for supporting an implant or prosthesis as claimed in claim 1, characterized in that the upper and lower rings are made of a biocompatible material of a metallic nature, preferably titanium or a titanium-based alloy.

3. The medical device for supporting an implant or prosthesis as claimed in claim 1, characterized in that the lower ring and the upper ring have openings that allow the device to be sutured to the surrounding tissues by surgery.

4. The medical device for supporting an implant or prosthesis as claimed in claim 1, characterized in that it also has an element situated under the lower ring and made of a rigid or semi-rigid biocompatible material, said element contributing to holding the device according to the invention in position.

5. The medical device for supporting an implant or prosthesis as claimed in claim 1, characterized in that the shape of the upper ring is selected in order to receive the shape of the implant or of the prosthesis for which it will provide the support, and in that said upper ring is equipped with a means for anchoring said implant or said prosthesis.

6. The medical device for supporting an implant or prosthesis as claimed in claim 5, wherein the anchoring means is selected from among a fixation system providing locking by rotation, by shrink-fit or force-fit assembly, by threading, by fixing with springs or clips, by lugs, by hoops, by countersinking or by interlocking.

7. The medical device for supporting an implant or prosthesis as claimed in claim 6, characterized in that the anchoring means is a system of clipping or fixing with springs.

8. The medical device for supporting an implant or prosthesis as claimed in claim 1, wherein the shape of the lower ring (2), and of the element (3) if need be, corresponds to the anatomical shape of the tissue for implantation of the device.

9. The medical device for supporting a tracheal implant or prosthesis as claimed in claim 1, wherein it is composed of two parts, one of which constitutes an upper ring made of a rigid or semi-rigid, solid biocompatible material, and the other of which constitutes a lower ring made of a rigid or semi-rigid, porous or integratable biocompatible material, said device being intended to receive an implant or a removable prosthesis at the upper ring and to be installed in situ on the trachea of the patient by means of the lower ring.

10. The medical device for supporting an implant or prosthesis as claimed in claim 9, wherein the upper ring and the element are made of solid titanium or of an alloy based on solid titanium, in that the lower ring is made of porous titanium or of an alloy based on porous titanium, and in that the ring and the element are equipped with openings to permit fixation by suturing to the tissues of the trachea.

11. The medical device for supporting an implant or prosthesis as claimed in claim 1, wherein the upper ring is of a grooved shape.

12. A kit for surgery of the larynx, comprising the medical device as claimed in claim 1, and a silicone tube having such an external diameter that it can be inserted into the lower ring of said device.

13. The kit for surgery of the larynx as claimed in claim 12, additionally comprising a removable element intended to be fixed to said medical device after implantation in the patient, said removable element being composed of a body made of biocompatible metal, and the upper part thereof having two concentric flaps, the first flap being able to drop, the second flap being able to lift, said flaps being rigidly connected at a hinge region, said flap being able not only to drop but also to lift together with the flap.

14. The kit as claimed in claim 13, wherein said device comprises a first anchoring means, and in that said removable element comprises an anchoring means cooperating with said first anchoring means in order to rigidly connect said removable element to said device.

15. The kit as claimed in claim 14, wherein said anchoring is reversible, said removable element being able to be disconnected from said device.

16. A prosthesis intended to be positioned on a device as claimed in claim 1, in order to replace the larynx of a patient, further comprising a body made of biocompatible metal, the upper part of which is provided with two concentric flaps, the first flap being able to drop, the second flap being able to lift, said flaps being rigidly connected at a hinge region, said flap being able not only to drop but also to lift together with the flap, said prosthesis additionally comprising means for anchoring on said device.

* * * * *